US011488697B1

(12) United States Patent
Falcone et al.

(10) Patent No.: US 11,488,697 B1
(45) Date of Patent: Nov. 1, 2022

(54) NETWORK ARCHITECTURE FOR STREAM-PARALLEL DATA AGGREGATION

(71) Applicant: Audacious Inquiry, LLC, Catonsville, MD (US)

(72) Inventors: Marc Falcone, Baltimore, MD (US); Chris Cimaszewski, Baltimore, MD (US); Matthew Carver, Hershey, PA (US); Travis Zimmerman, Rocky Mount, VA (US); Jon Clark, Summerville, SC (US); Samit Desai, Baltimore, MD (US); Ed VanBaak, Boulder, CO (US)

(73) Assignee: Audacious Inquiry, LLC, Catonsville, MD (US)

( * ) Notice: Subject to any disclaimer, the term of this patent is extended or adjusted under 35 U.S.C. 154(b) by 0 days.

(21) Appl. No.: 17/518,317

(22) Filed: Nov. 3, 2021

(51) Int. Cl.
  *G16H 10/60* (2018.01)
  *G06F 16/2455* (2019.01)
  *G16H 20/40* (2018.01)

(52) U.S. Cl.
  CPC ......... *G16H 10/60* (2018.01); *G06F 16/2455* (2019.01); *G16H 20/40* (2018.01)

(58) Field of Classification Search
  CPC ..... G16H 10/60; G16H 20/40; G06F 16/2455
  USPC ....................................................... 702/2, 3
  See application file for complete search history.

(56) References Cited

U.S. PATENT DOCUMENTS

| 8,682,993 | B1 * | 3/2014 | Bell ....................... G16Z 99/00 709/206 |
| 9,083,770 | B1 | 7/2015 | Dröse et al. |
| 9,348,876 | B1 | 5/2016 | Paranjpe et al. |
| 9,437,022 | B2 | 9/2016 | Vander Broek |
| 9,800,608 | B2 | 10/2017 | Korunsky et al. |
| 10,938,962 | B2 | 3/2021 | Howard et al. |
| 11,114,194 | B2 | 9/2021 | Antony et al. |
| 11,252,209 | B1 * | 2/2022 | Watanabe ........... H04L 65/4069 |

(Continued)

FOREIGN PATENT DOCUMENTS

| KR | 20140071041 A | * | 6/2014 | ............. G16H 10/00 |
| WO | WO-2015009541 A1 | * | 1/2015 | ............ G06F 19/321 |

OTHER PUBLICATIONS

Thomas Moore et al., "Event Detection: A Clinical Notification Service on a Health Information Exchange Platform" AMIA Annu Symp Proc. 2012; 2012: 635-642. (Year: 2012).*

*Primary Examiner* — Joshua B Blanchette
(74) *Attorney, Agent, or Firm* — Ryan Alley IP

(57) ABSTRACT

A parallel network architecture connects among providers, subscribers, and storage networks to pull clinical records in an automated and verifiable electronic context. Messages, alerts, or data updates from a healthcare event such as a discharge are received, and example embodiment networks calculate patient clinical data target from the same and query the target for the patient to solicit records for the patient of the event, proximate to the event. The received records may be clinical, with diagnostic and treatment records for the patient, to be automatically delivered back to a subscribing user. Example embodiment networks may improve record quality and data match by verifying a target stores records for the patient, timing queries and requested data to those found most successful for a target, and/or not delivering records that contain errors, no clinical data, are duplicative or unreadable, and/or are not for the patient or healthcare event.

17 Claims, 3 Drawing Sheets

(56) References Cited

U.S. PATENT DOCUMENTS

| | | |
|---|---|---|
| 2014/0324480 A1 | 10/2014 | Dufel et al. |
| 2014/0358585 A1 | 12/2014 | Reiner |
| 2015/0161413 A1 | 6/2015 | Calem et al. |
| 2015/0242568 A1 | 8/2015 | Antony et al. |
| 2015/0242569 A1 | 8/2015 | Antony et al. |
| 2015/0242574 A1 | 8/2015 | Antony et al. |
| 2016/0034641 A1 | 2/2016 | Antony et al. |
| 2016/0063191 A1 | 3/2016 | Vesto et al. |
| 2016/0283667 A1 | 9/2016 | Rachapalli et al. |
| 2017/0161439 A1* | 6/2017 | Raduchel ................ G06F 21/31 |
| 2017/0220742 A1* | 8/2017 | Antony .................. G16H 10/60 |
| 2017/0235890 A1 | 8/2017 | Chen et al. |
| 2019/0172590 A1 | 6/2019 | Vesto et al. |
| 2020/0312458 A1 | 10/2020 | Luna et al. |
| 2021/0057064 A1* | 2/2021 | Ballard .............. G06Q 10/1095 |
| 2021/0194997 A1 | 6/2021 | Antony et al. |
| 2022/0157420 A1 | 5/2022 | Cross et al. |

\* cited by examiner

NETWORK ARCHITECTURE FOR STREAM-PARALLEL DATA AGGREGATION

BACKGROUND

FIG. 1 is an illustration of a related art network interaction between care manager 60 and a large-area or large-client network 15, such as a national database that is a repository for thousands or millions of electronic health records. As shown in FIG. 1, at a first time T1, patient 10 receives treatment or other clinical interaction from healthcare provider 50. Typically, following treatment, such as at discharge or in an after-visit write-up, provider 50 generates a clinical electronic record that captures treatment details for patient 10. This may include lab results, clinician notes, a discharge summary document, standardized summary of care messages, etc. that capture some aspect of the physical healthcare administered and clinical condition of patient 10 in an electronic format. Provider 50 may do any number of things with this electronic record at discharge, including saving it with no further action, providing it to a regional or national network like a healthcare information exchange, sending it to an insurer or government regulator, and/or, rarely, providing it to care manager 60 having an affiliation with provider 50. In the much more common instance that care manager 60 is unaffiliated with provider 50 or simply lacks a record-sharing relationship, care manager 60 receives no clinical health records for patient 10 or even administrative notifications of the discharge or other indication anything happened at T1.

Then, at T2, at some time after T1, potentially weeks or months, care manager 60 becomes aware of patient 10 and their interaction with provider 50. For example, care manager 60 may be a primary care physician or an insurer to whom patient 10 presents for follow-up care, reimbursement, or an entirely separate healthcare encounter well after T1. Care manager 60 must then attempt to gather the electronic health records reflecting the discharge and treatment at T1. In FIG. 1, this gathering occurs at T3, after T2, and may require several searches across different network portals and electronic health record systems by manager 60. Several different requests may need to be made over time as data becomes entered and available through repository network 15. Differing standards and poor identification matches for patient 10 will often further delay or make impossible location of treatment details from repository network 15. Care manager 60 may be required to pay for each pull or gather of documents from each repository network 15 queried.

Even later, at T4, repository network 15 may provide solicited clinical treatment documents back to care manager 60. These documents may be provided over a time-consuming medium such as postal mail or fax, often delayed from the query at T3, such as when care manager 60 is unavailable. Finally, later at T5 care manager 60 can make informed treatment of or other reformed response to patient 10, usually by scheduling a new appointment or ordering a new test or treatment even after T4 when solicited care documents are received. The total amount of time, actors, and individual actions/retries across all of T1-T5 may require several weeks or months, if any correct record is delivered and utilized at all.

SUMMARY

Example embodiments include network architectures and methods of configuring and operating networks connected between data streams and sources, end users, and electronic record stores and third-party networks to provide fast, automatic, and correct data responses. Example embodiment networks interface with data sources to receive electronic patient information, potentially in a curated manner, such as down to only discharge-type HL7 ADTs. From this information, example embodiment networks are programmed to compute in real time a patient identification and target for retrieving electronic medical records for the patient, such as a national network, record database, or other health record source. Determining the patient and target, example networks may automatically query the target for the patient with accurate terms to solicit record retrieval and delivery for the patient, in a useful timeframe from the electronic patient information being created and/or a healthcare event for the patient. The received records may include thorough clinical data and media for the patient, which may then be automatically delivered back to a subscribing user. Example embodiment networks may also take accuracy and verification measures on the records, such as by verifying a target recognizes a patient, delaying a query or request type based on target identity, and/or discarding lower quality records that contain errors, lack clinical data, are redundant, and/or do not well match a patient or healthcare event.

BRIEF DESCRIPTIONS OF THE DRAWINGS

Example embodiments will become more apparent by describing, in detail, the attached drawings, wherein like elements are represented by like reference numerals, which are given by way of illustration only and thus do not limit the example embodiments herein.

DETAILED DESCRIPTION

Figure 1:
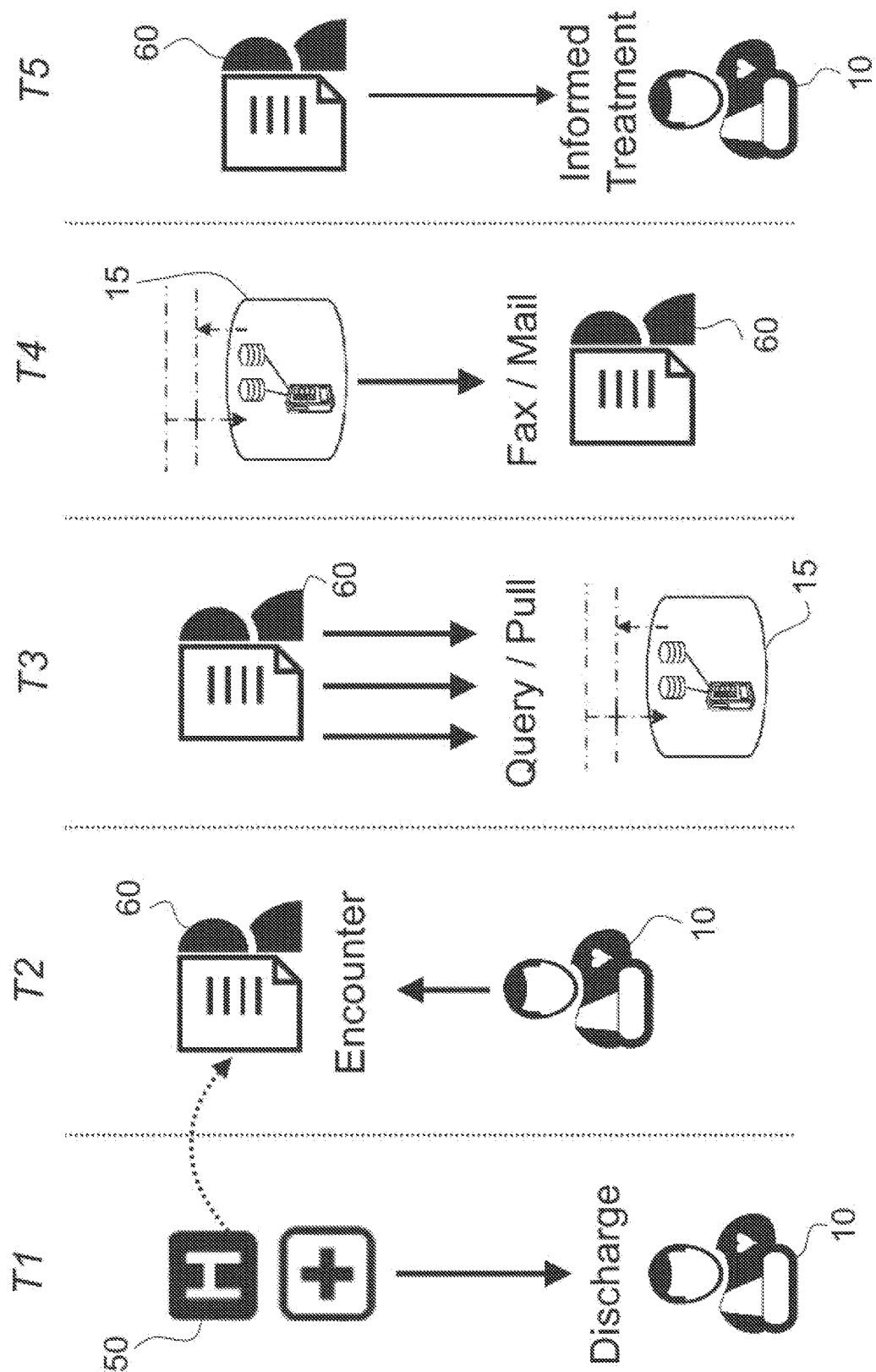
FIG. 1 is an illustration of a related art care manager record gathering interaction.

Because this is a patent document, general broad rules of construction should be applied when reading it. Everything described and shown in this document is an example of subject matter falling within the scope of the claims, appended below. Any specific structural and functional details disclosed herein are merely for purposes of describing how to make and use examples. Several different embodiments and methods not specifically disclosed herein may fall within the claim scope; as such, the claims may be embodied in many alternate forms and should not be construed as limited to only examples set forth herein.

Modifiers "first," "second," "another," etc. may be used herein to describe various items, but they do not confine modified items to any order. These terms are used only to distinguish one element from another; where there are "second" or higher ordinals, there merely must be that many number of elements, without necessarily any difference or other relationship. For example, a first element could be termed a second element, and, similarly, a second element could be termed a first element unless an order or difference is stated. In listing items, the conjunction "and/or" includes all combinations of one or more of the associated listed items. The use of "etc." is defined as "et cetera" and indicates the inclusion of all other elements belonging to the same group of the preceding items, in any "and/or" combination(s).

When an element is related, such as by being "connected," "coupled," "mated," "attached," "fixed," etc., to another element, it can be directly connected to the other element, or intervening elements may be present. In contrast, when an element is referred to as being "directly connected," "directly coupled," etc. to another element, there are no intervening elements present. Other words used to describe the relationship between elements should be interpreted in a like fashion (e.g., "between" versus "directly between," "adjacent" versus "directly adjacent," etc.).

When describing electronic devices, a term such as "communicatively connected" includes all variations of information exchange and routing between two devices, including intermediary devices, networks, etc., connected wirelessly or not. Similarly, when describing computerized networks, the term "real time" and the like takes on its plain meaning, including operations executed at a speed and volume beyond human execution, such as two events that would require discrete human actions over time occurring in direct sequence or simultaneously to human perception.

As used herein, singular forms like "a," "an," and "the" are intended to include both the singular and plural forms, unless the language explicitly indicates otherwise. Indefinite articles like "a" and "an" introduce or refer to any modified term, both previously-introduced and not, while definite articles like "the" refer to the same previously-introduced term. Possessive terms like "comprises," "includes," "has," or "with" when used herein, specify the presence of stated features, characteristics, steps, operations, elements, and/or components, but do not themselves preclude the presence or addition of one or more other features, characteristics, steps, operations, elements, components, and/or groups thereof. Rather, exclusive modifiers like "only" or "singular" may preclude presence or addition of other subject matter in modified terms.

The structures and operations discussed below may occur out of the order described and/or noted in the figures. For example, two operations and/or figures shown in succession may in fact be executed concurrently or may sometimes be executed in the reverse order, depending upon the functionality/acts involved. Similarly, individual operations within example methods described below may be executed repetitively, individually or sequentially, so as to provide looping or other series of operations aside from single operations described below. It should be presumed that any embodiment or method having features and functionality described below, in any workable combination, falls within the scope of example embodiments.

The inventors have recognized that related methods of pulling clinical data from electronic repositories often includes large amounts of manual entry by care providers, is often executed outside of effective timeframes, and provides inconsistent or incorrect results. Providers often do not have full or correct information or know where specifically to solicit clinical post-discharge documents, resulting in poor matching and information provided. For example, the lag between a discharge and a care manager or provider actually knowing about and soliciting clinical documents from a correct source about the patient being discharged may be so large that information eventually delivered is outdated or incorrect, as intervening encounters and discharges may occur. Querying of incorrect sources and/or with limited patient data may result in no, old, and/or incorrect clinical documents being provided. Similarly, because even delivery of responsive documents to a correct request may take days or weeks, a care manager or provider must delay care beyond an initial encounter to make informed treatment, potentially causing even more intervening discharges for the patient, or potentially proceed with uninformed care that may pose worse health outcomes. Even further, because different networks or exchanges work on different querying information and document standards, care providers may have inconsistent experiences between records and fail to understand or be able to read documents provided in unfamiliar formats. To overcome these newly-recognized problems as well as others, the inventors have developed example embodiments and methods described below to address these and other problems recognized by the Inventors with unique solutions enabled by example embodiments.

The present invention is a network architecture and methods of operating the same. In contrast to the present invention, the few example embodiments and example methods discussed below illustrate just a subset of the variety of different configurations that can be used as and/or in connection with the present invention.

Figure 2:
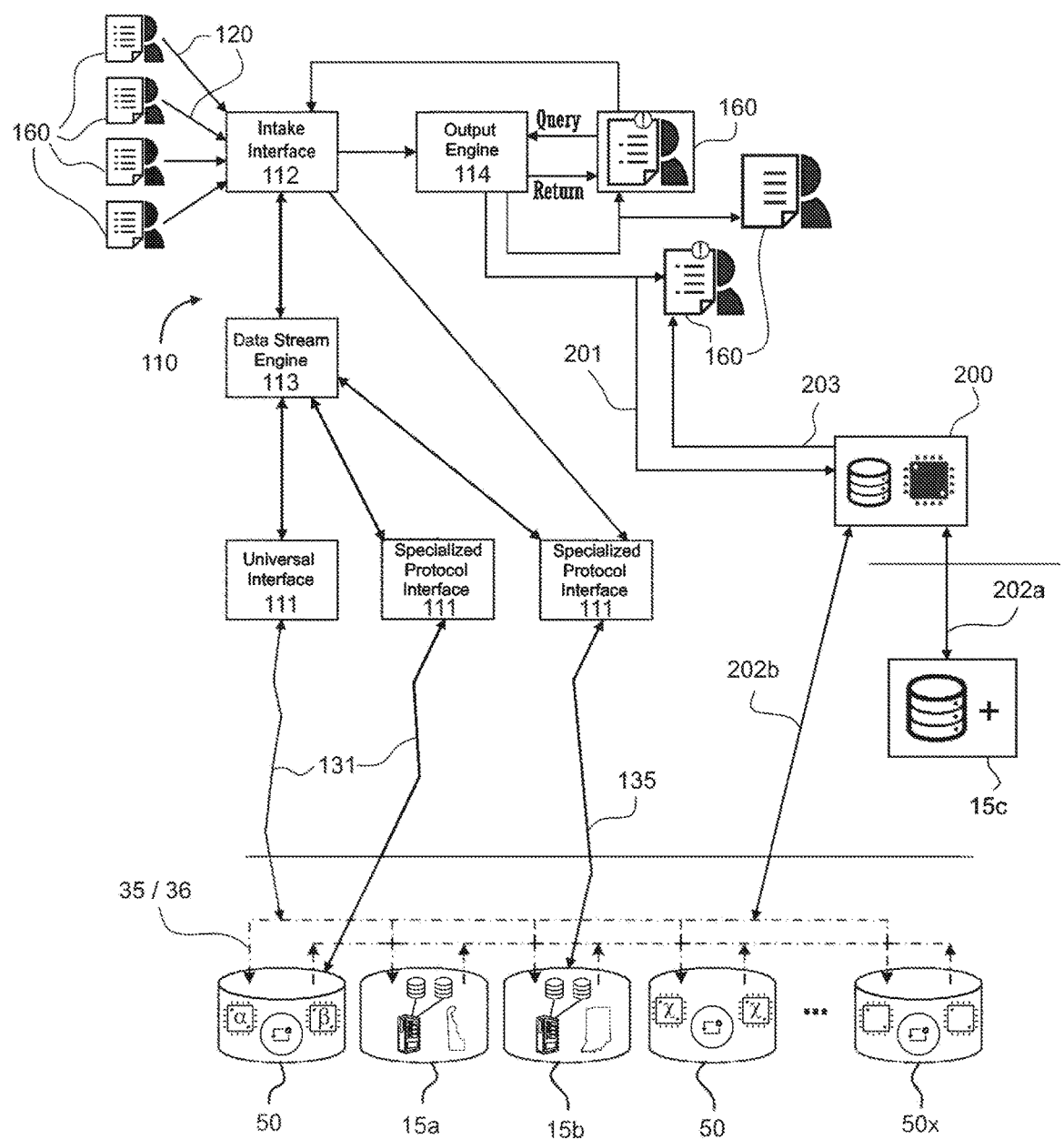
FIG. 2 is an illustration of an example embodiment network architecture including an example embodiment aggregator.

FIG. 2 is an illustration of an example embodiment network architecture, or network, for data aggregation alongside multiple disparate data streams, sources, and/or feeds. Several features of the example embodiment network of FIG. 2 are described in US Patent Publication 2021/0194997 to Antony et al. published Jun. 24, 2021 and incorporated herein by reference in its entirety. Example embodiment aggregator 200 may work with the remainder of this network from the incorporated '997 publication. For example, as shown in FIG. 2, example embodiment aggregator 200 may be interfaced with cluster 110, such as at output engine 114, and with subscribers 160, as well as data sources 50 and exchanges 15 over interfaces 201, 202, and 203.

Example embodiment aggregator 200 includes a computer processor and configured memory that are programmable to execute example methods described below. Aggregator 200 may be a module with control of processing and storage resources within cluster 110, or aggregator 200 may be a separate server, computer, or other processor-based system remote from, and even separately operated from, the remainder of the network of FIG. 2. Example embodiment aggregator 200 may further be operated as a stand-alone system interfaced only with subscribers 160, data sources 50, and/or exchanges 15, without the remainder of the network of FIG. 2, by simply including the necessary interfaces for reading and parsing incoming data from the sources in multiple formats.

Example embodiment aggregator 200 is communicatively connected with a repository exchange 15c, which may be a large-scale separate network of electronic health records (EHRs) potentially in multiple formats and standards from multiple difference sources. For example, repository exchange 15c may be a nation- or industry-wide network connected among many individual electronic medical record systems storing huge amounts of EHRs sent from many providers for many patients over time. Repository exchange 15c collectively may store hundreds of millions of EHRs from hundreds of thousands of medical providers like hospitals and clinics, pharmacies, laboratories, government agencies, etc. For example, repository exchange 15c may be an existing nationwide network like eHealth Exchange™, Carequality®, and commonwell Health Alliance®. In contrast to smaller and basic administrative messages, repository exchange 15c may store and/or have access to clinical documents detailing healthcare treatment administered, potentially with rich media and care information like diagnoses, medicines administered, tests ordered, progression through recovery, procedures, detailed patient vitals, prescriptions, and/or other health conditions.

Interface 202a between aggregator 200 and repository exchange 15c may be fully integrated and/or automated, such as through an API call, with aggregator 200 having all permissions and credentials to search, read, retrieve, and/or write records from/to repository exchange 15c. Interface 202a may be configured to operate in any format of exchange 15c, and payment or relationship between operators of aggregator 200 and repository exchange 15c may permit aggregator 200 to use interface 202a to so search, read, retrieve, write, etc. from/to repository exchange 15c in larger volumes to both test for and pull relevant clinical documents. For example, interface 202a could use a Direct, HL7, SOAP, RESTful, XCPD, FHIR, etc. format adapted for each repository exchange 15c, based on the exchange's operating protocols and/or access relationship with aggregator 200.

Example embodiment aggregator 200 may otherwise be configured to coordinate data from interfaces 201, 202, and 203. For example, aggregator 200 may be communicatively connected over interface 201 to output engine 114 that provides specific, filtered standardized administrative messages reflecting a discharge or other information. Aggregator may further be communicatively connected over interface 203 to subscribers 160 for delivery of coordinated data and/or over interface 202 to gather clinical or administrative data from the multiple sources and streams shown in FIG. 2.

Figure 3:
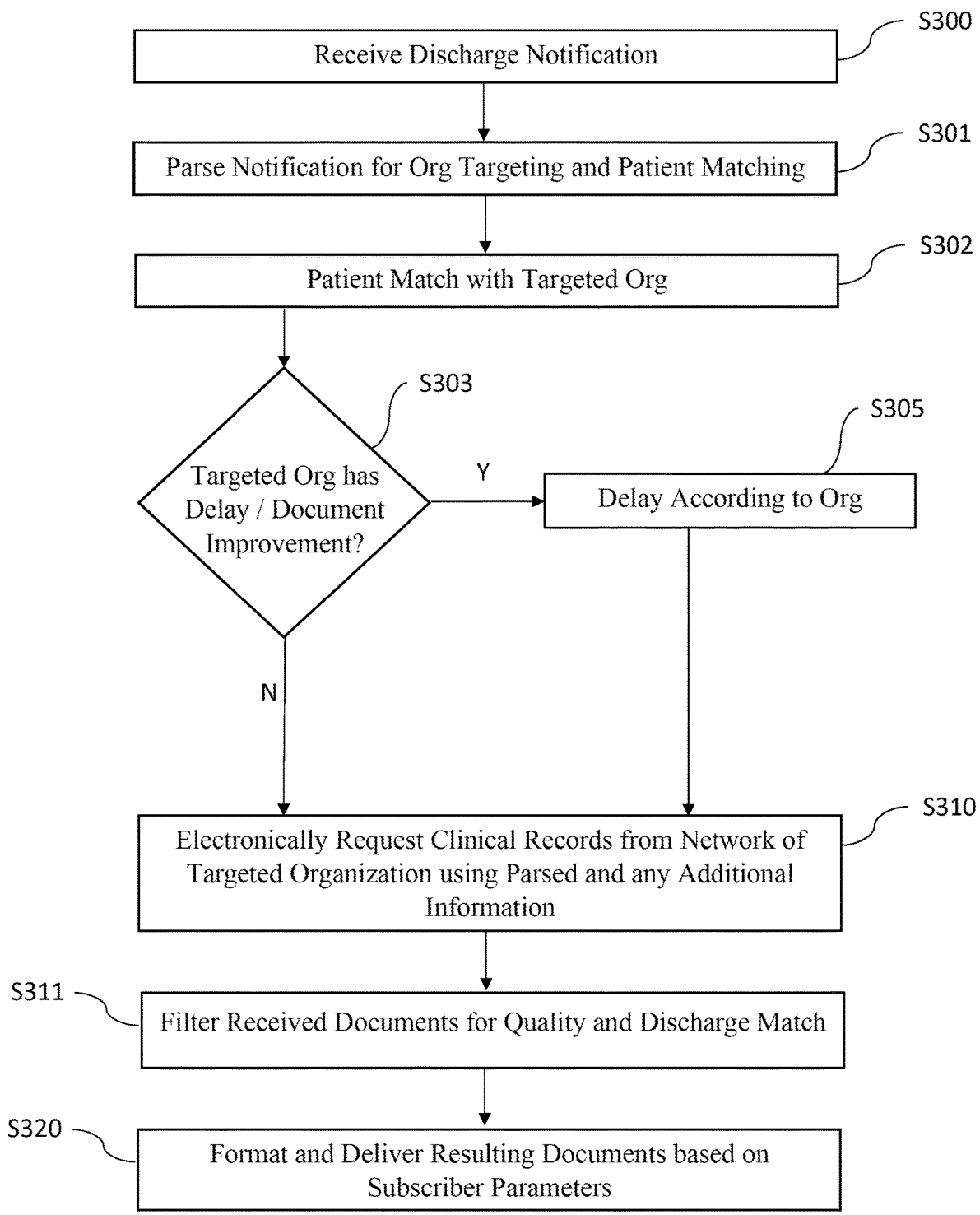
FIG. 3 is a flow chart illustrating an example method with which an example embodiment aggregator may be configured.

FIG. 3 is a flow chart illustrating an example method of how a network architecture, including example embodiment aggregator 200 of FIG. 2, may execute and adjust operations based on information flow. For example, a processor of aggregator 200 may be programmed and/or physically configured to execute the actions of FIG. 3 as a specifically configured network architecture.

In S300, a discharge notification is received. Similar to actions taken at discharge at T1 of FIG. 1, a healthcare provider may further electronically generate some administrative indication of completed treatment. In S300 this indication is received by the aggregator as a discharge notification. If aggregator 200 is communicatively connected to cluster 110 from FIG. 2 or the like, such discharge notifications may be screened to reflect accurate discharges in real time and be well-fitted to subscribers 160. For example, as described in the incorporated '997 publication, cluster 110 may coordinate and filter data streams and feeds from multiple, potentially hundreds of thousands, of sources in different formats, and filter for discharge-type flags in a variety of administrative messages for selective and efficient forwarding to aggregator 200. For example, when screening Health Level 7 (HL7) Admit Transfer Discharge (ADT) messages, output engine 114 may provide an HL7 ADT message with an A03 field reflecting a discharge of a patient from a roster of a subscriber 160 in real time with the care provider generating the ADT. Other HL7 CCDA messages, Direct messages, and other administrative and clinical electronic messages indicating discharge may be received at S300. It is equally possible for the discharge notification to be received directly from a provider or source without any filtering or screening by intermediary cluster 110 or otherwise.

With an electronic discharge notification received in S300, the notification can be parsed for extraction of data that determines where and how clinical documents for the patient matching that discharge can be found in S301. This may include de-encrypting, de-compressing, translating, exploding, and/or filtering the notification according to its type, format, standard, etc. Any aggregator configured to execute S301 must be programmed or formatted to so read and extract useful data in the received notification's format or formats. Desired information from the notification may include patient identification, medical record numbers, organization identifier, healthcare provider identification, patient demographic data, and other basic identifiers that may be present in even simple administrative electronic messages like a discharge-type HL7 ADT for example. For example, an aggregator may read out a patient medical record number and care provider organizational ID from specific fields in a discharge-type HL7 ADT in S301. This information parsed in S301 may directly identify a network to be targeted, or may correspond to identifiers for a network likely to have responsive clinical documents.

In S302, the aggregator may query the determined network based on the information extracted in S301, to test if the patient has electronic records in that network. That is, the aggregator may be communicatively connected among several different exchanges 15, and only one may have correct or best clinical data reflecting healthcare administered for the discharge notification. For example, making a guess for the best-fit organization from org ID extracted from a discharge notification in S301, the aggregator may query the guessed repository network 15c with an extracted patient ID, and the repository network may return a patient found/not found message.

Additionally, in S301 and S302, other data sources, including databases in cluster 110, exchanges 15a, 15b, and/or sources 50, including a master patient index, may be used to match and determine patient identification, organization identifier, healthcare provider identification, patient demographic data, etc. from information received in the discharge notification. This may better ensure a proper patient is identified and a correct organization is targeted and queried in S302 and S310. For example, cluster 110 and/or aggregator 200 may generate and/or store a list of known repository exchanges 15c for each healthcare provider source 50 that generates discharge notifications. Knowing the provider and all corresponding patient and discharge information may permit not only a correct network to be targeted for querying, but also ensure operable or most successful identifying information is used in the query to solicit accurate records for the discharge. This matching and/or correction may be pursued before or after receiving any error, such as a not found message from a targeted organization network in S301, which may suggest some error in the discharge notification alone that caused an incorrect network to be targeted for query or incorrect patient identifying information to be used.

All of S300-S302 can be performed in real time with generation of a discharge notification from a healthcare provider, such that identification of a source of clinical documents for the discharged patient may be immediate. It may be beneficial to delay any of S300-S302 and/or the actual request for clinical documents in S310, because full or useful clinical documents may require additional processing, delivery, or generation time, especially compared to real time generation of an administrative discharge notification. In S303, a delay for the request for clinical documents may be determined. For example, aggregator 200 may store or have access to a database associating most successful or otherwise desired delay periods and document types with targeted organizations' networks. Table 1 shows an example of fields in such a database.

TABLE 1

| Targeted Network Organization | Delay | Document Type(s) |
| --- | --- | --- |
| Hospital A | 12 hrs | Progress Note |
| Hospital B | 3 hrs | Summary of Episode, Discharge Summary |
| Exchange A | 24 hrs | Hospital Discharge Summary |
| Exchange B | 15 hrs | Care Record Summary, Discharge Summary |
| National Network A, EMRS 1 | None | CCDA-Discharge-Summary |
| National Network A, EMRS 2 | 72 hrs | Any |
| National Network B | 6 hrs | CCDA |
| State Database A | None | Any |
| State Database B | 48 hrs | Progress Note, Subsequent Evaluation Note |

The values in delay and document type for each targeted network may be provided by the organization operating the same, manually input, and/or determined through iterative testing any record source as a target. For example, aggregator 200 may repeatedly request documents known to exist that provide details for a known patient's discharge from various targets including care providers, exchanges, regional/national repositories, and/or individual stores and providers within such networks, at various time intervals and by various document names and/or types. Success rates at each time and/or for each document are recorded. Then, time periods and document names/types associated with most successful retrievals are stored for that target, such that a database resembling Table 1 can be built for hundreds or thousands of different targets, including potentially all targeted networks and information sources by aggregator 200.

In S303, the aggregator can consult the database for a targeted organization in real time with receipt of a discharge notification, and if a delay period for the target exists in S305, wait the indicated interval before proceeding to S310. If no delay interval is indicated or no entry for the organization exists, a default delay may be executed, or the remainder of S310-S320 may be executed in real time.

In S310, the clinical documents for the patient corresponding to the discharge notification are requested from the targeted network. This query may be following a delay in S305 for the targeted network, and the query may solicit known responsive documents for the verified patient of the network, based on any document types listed for the target in Table 1. For example, in S310 the aggregator may request documents for a patient ID associated with a medical record number extracted from a discharge notification that is compatible with the targeted source, in a document format tested and stored to be successful for the target, to maximize likelihood of query and delivery of responsive documents. The queried documents are delivered, such as through automatic, electronic means to aggregator 200, which may then store the received documents in a local or remote storage. Any authentication, payment, encryption, and/or communication protocol is established through an interface between the network and aggregator, such as interface 202*a*.

In S311, the received documents may be verified for quality and to ensure they correspond to treatment that led to the discharge underlying the received notification in S301. For example, the aggregator may discard corrupt, duplicate, or incorrect documents, as well as documents of lower value among several received. Correspondence may be verified by parsing the documents for a creation timestamp that is within a timeframe of the discharge from the discharge notification. For example, comparing times between received documents and discharge times whose differences are outside of several hours of one another or not on a same day may result in those documents being withheld or discarded. Basic, administrative details like patient demographics or high-level diagnosis or condition may also be compared between received documents and discharge notification to verify responsiveness and filter wrong or lower-quality documents. The received clinical documents may also be parsed to ensure a full diagnosis and administered medications are included, potentially in addition to all other healthcare administered, including tests and labs.

In S320, the verified, potentially corrected documents are provided to subscribers in accordance with their provided parameters. For example, aggregator 200 may provide the documents in a desired format, such as HTML or PDF, to subscribers 160 via email, FTP, and EHR API or any other endpoint specified by subscriber 160. This may include conversion of machine-readable standard documents such as CCDAs into human-readable documentation. Each subscribers' parameters for delivery may be provided directly to aggregator 200 by subscriber 160, or cluster 110 may provide the parameters along the with triggering discharge notification. For example, cluster 110 may be configured to operate as the examples of any of the '997 publication, US Patent Publication 2017/0098043, published Apr. 6, 2017 to Antony et al., US Patent Publication 2017/0220742, published Aug. 3, 2017 to Antony et al., US Patent Publication 2016/0034641, published Feb. 4, 2016 to Antony et al., US Patent Publication 2015/0242569, published Aug. 27, 2015 to Antony et al., US Patent Publication 2015/0242568, published Aug. 27, 2015 to Antony et al., and US Patent Publication 2015/0242574, published Aug. 27, 2015 to Antony et al., all of which are incorporated herein by reference in their entireties. In this way, cluster 110 may coordinate both alerts of discharge activity to subscribers for responsive patients, while aggregator 200 solicits and provides clinical discharge documents to the same matching subscribers for the responsive patients.

The example method of FIG. 3 may automatically and timely aggregate clinical documents that correctly correspond to treatment of a discharged patient and provide the same to a care manager for informed treatment as soon as the next patient encounter with that manager. The care manager does not have to wait for the patient to present, does not have to gather identification information for the patient to query a national database or repository, does not have to attempt multiple different such queries, and does not have to wait for delivery of responsive documents in formats out of the provider's control. By eliminating a subscriber or provider's involvement and leveraging administrative discharge data to trigger in real time robust matching and/or querying of targeted sources, example methods and networks configured to execute the same thus ensure informed and timely treatment post-discharge is more likely.

As with all healthcare information sharing among separate parties, appropriate safeguards—including encryption, encoding, and/or communications protocols—may be placed on any interface and transmission in example embodiments and methods. It is understood that ANSI X12, Direct, and HL7 protocols are defined by their standard-setting bodies, explained at x12.org; and h17.org/implement/standards, incorporated herein by reference in their entireties, with current and future editions of these standards included in those terms. Similarly, because providers, HIEs, subscribers, patients, and networks can all be distinct actors with independent owners and operators with distinct interests, appropriate consents and HIPAA-compliant releases may be secured or required from each independent party before any information exchanging or usage is executed in any example.

Actions throughout example embodiment network architectures may include user authentication, data verification, privacy controls, and/or content screening. This will also extend to use an authentication key or access key or device-based unique key or any combination thereof. In this way, one or more operators can be blocked or denied access. For example, operators and other parties may never be provided with identifying information of one another, such that a party creating entries in a data stream, a party operating as an electronic healthcare record repository, and/or a party consuming the same may remain anonymous to the other. Data may be encrypted and not retained at one or all points in example methods, such that there may be no discoverable record of signals from data streams, independent media, origin and/or limitation information in regard to such content, existence, performance, etc.

Encryption includes one or more aspects of authentication, entitlement, data integrity, access control, confidentiality, segmentation, information control, and combinations thereof. Encryption can be accomplished using any encryption technology, such as the process of converting digital information into a new form using a key or a code or a program, wherein the new form is unintelligible or indecipherable, and includes encoding, compressing, or any other translating of the digital content. Encryption of the digital media content can be performed in accordance with any technology including utilizing an encryption algorithm. The encryption algorithm utilized is not hardware dependent and may change depending on the digital content. For example, a different algorithm may be utilized for different websites or programs.

As to verification, example networks and methods may take advantage of an operator login model requiring user authentication with a password over a secured connection and/or using operating-system-native security control and verification on communications devices, to ensure only verified, permitted operators gain access. Example embodiment network architectures may also require payment verification, such as credit card or bank account authentication, to verify identity and/or ability to pay before allowing access and may use location and input verification available through operating system controls or other network functionalities, potentially in combination with user feedback, to prevent or punish location spoofing, user account compromising, bot access, and/or harassment or waste.

Example embodiment networks and methods can be made accessible through a portal or an interface which is a part of, or may be connected to, an internal network or an external network, such as the Internet or similar portal. The portals or interfaces are accessed by one or more of users through an electronic device, whereby the user may send and receive signals to the portal or interface which gets stored in at least one memory device or at least one data storage device or at least one server. The configuration described herein may be optionally executed from functional data structures on one or more of a non-transitory, computer readable medium, in relation with, and in combination with such pieces of hardware. Such executable configurations may include a website, an executable software program, and/or a software application. A non-transitory, computer readable medium may include media such as magnetic storage medium (e.g., hard disk drives, floppy disks, tape, etc.), optical storage (CD-ROMs, DVDs, optical disks, etc.), volatile and non-volatile memory devices (e.g., EEPROMs, ROMs, PROMs, RAMs, DRAMs, SRAMs, Flash Memory, firmware, programmable logic, etc.), etc. The code implementing the described operations may further be implemented in hardware logic (e.g., an integrated circuit chip, Programmable Gate Array (PGA), Application Specific Integrated Circuit (ASIC), etc.).

An operator may provide user input through any suitable input device or input mechanism such as but not limited to a keyboard, a mouse, a joystick, a touchpad, a virtual keyboard, a virtual data entry user interface, a virtual dial pad, a software or a program, a scanner, a remote device, a microphone, a webcam, a camera, a fingerprint scanner, a cave, pointing stick, etc. Communicative connections and control among network structures may use TCP/IP, Bluetooth, Wi-Fi, Wimax, near-field communications, optical signals, etc.

Some examples described here, it is understood that one or more example methods may be used in combination and/or repetitively to produce multiple options and functionalities for operators of networks connected among several different types of records and repositories through proper computer programming or hardware configuring of networks and communications devices to perform example EHR aggregation, at any number of different processor-based devices that are communicatively connected. Example methods and embodiments thus being described, it will be appreciated by one skilled in the art that example embodiments may be varied through routine experimentation and without further inventive activity. Variations are not to be regarded as departure from the spirit and scope of the exemplary embodiments, and all such modifications as would be obvious to one skilled in the art are intended to be included within the scope of the following claims.

What is claimed is:

1. A network connected between a plurality of data sources, subscribers, and electronic health record repositories, the network comprising:
    a notification interface networked with the plurality of data sources, wherein the plurality of data sources provide information in real time and in a plurality of different formats, and wherein the notification interface is configured with the plurality of different formats to electronically receive a discharge notification for a patient from the information provided by the data sources regardless of format;
    a plurality of repository interfaces configured to electronically query and receive data from the records repositories;
    a persistent memory configured to store the data; and
    a processor coupled with the persistent memory and repository interfaces, wherein the processor is configured with memory storing instructions that when executed cause the processor to,
        receive and parse the discharge notification for patient and organizational identifiers,
        associate the patient and organization identifiers with query terms and a record repository of the record repositories in real time with generation of the discharge notification,
        query the record repository with the query terms, receive the data from the record repository, wherein the data includes clinical documents describing treatment of the patient, verify the clinical documents correspond to the patient and a discharge of the discharge notification, wherein the verifying includes comparing a creation time of the clinical documents to a time of the discharge notification and not electronically providing the clinical documents outside of a time threshold determined by the comparing, and electronically provide the verified clinical documents to a subscriber who has previously identified the patient to the network.

2. The network of claim 1, wherein the discharge notification includes at least a portion of a discharge-type Health Level 7 (HL7) Admit-Discharge-Transfer (ADT) message generated by a facility discharging the patient.

3. The network of claim 1, wherein the instructions further cause the processor to,
determine a delay period for the record repository, and
query the record repository only after the delay period.

4. The network of claim 3, wherein the delay period is determined from a database associating the record repositories each with a delay period determined from previous sampling of response success from the associated record repository.

5. The network of claim 1, wherein the instructions further cause the processor to,
determine a document type for the record repository, and
query the record repository with the query terms including the document type.

6. The network of claim 5, wherein the document type is determined from a database associating the record repositories each with a document type determined from previous sampling of response success from the associated record repository.

7. The network of claim 1, wherein the record repository is at least one nationwide network.

8. The network of claim 1, wherein the associating the patient and organization identifiers with the query terms and the record repository includes verifying at least one of the record repositories recognizes a patient ID extracted from the notification.

9. A method of configuring network connections between a plurality of data sources, subscribers, and electronic health record repositories, the method comprising:
receiving and parsing, from the plurality of data sources with a processor networked with the plurality of data sources, a discharge notification for patient and organizational identifiers, wherein the plurality of data sources provide information in real time and in a plurality of different formats, and wherein the processor is configured with the plurality of different formats to receive and parse the discharge notification for the patient and organizational identifiers from the information provided by the data sources regardless of format;
associating, with the processor, the patient and organization identifiers with query terms and a record repository of the record repositories in real time with generation of the discharge notification;
querying, with the processor, the record repository with the query terms;
receiving and storing the data, in a persistent memory, from the record repository, wherein the data includes clinical documents describing treatment of the patient;
verifying, with the processor, the clinical documents correspond to the patient and a discharge of the discharge notification, wherein the verifying includes comparing a creation time of the clinical documents to a time of the discharge notification and not electronically providing the clinical documents outside of a time threshold determined by the comparing; and
electronically providing, with the processor, the verified clinical documents to a subscriber who has previously identified the patient to the network.

10. The method of claim 9, wherein the discharge notification includes at least a portion of a discharge-type Health Level 7 (HL7) Admit-Discharge-Transfer (ADT) message generated by a facility discharging the patient.

11. The method of claim 9, further comprising:
determining, with the processor, a delay period for the record repository, wherein the querying is executed only after the delay period.

12. The method of claim 11, wherein the delay period is determined from a database associating the record repositories each with a delay period determined from previous sampling of response success from the associated record repository.

13. The method of claim 9, further comprising:
determining, with the processor, a document type for the record repository, wherein the querying includes querying the record repository with the query terms including the document type.

14. The method of claim 13, wherein the document type is determined from a database associating the record repositories each with a document type determined from previous sampling of response success from the associated record repository.

15. The method of claim 9, wherein the record repository is at least one nationwide network.

16. The method of claim 9, wherein the associating the patient and organization identifiers with the query terms and the record repository includes verifying at least one of the record repositories recognizes a patient ID extracted from the notification.

17. A network connected between a plurality of parallel streams and users to condition and route the streams, the network comprising:
a protocol interface connected to the plurality of streams, wherein the plurality of streams provide information in real time and in a plurality of different protocols and include at least one Health Level 7 (HL7) Admit Discharge Transfer (ADT) message stream, wherein the protocol interface is configured for different protocols including HL7 to receive and parse the information provided by the streams regardless of format;
an intake interface configured to receive parameters for network operation on the plurality of streams from a plurality of users separate from the plurality of streams; and
a processor and memory coupled to the intake interface and protocol interface, wherein the memory includes instructions that when executed by the processor, cause the processor to,
limit flow of the plurality of streams to a receiving user of the plurality users to only at least a portion of an HL7 ADT message, wherein the at least the portion of the HL7 ADT message complies with the parameters for network operation for the receiving user, wherein the limiting is executed in real-time with the streams,
parse the at least the portion of the HL7 ADT message for an identifier of a patient and an organization, associate the patient and organization identifiers with query terms and a record repository of the record repositories in real time with the streams, query the record repository with the query terms, receive the data from the record repository, wherein the data includes clinical documents describing treatment of the patient, electronically provide the verified clinical documents to the receiving user, and verify the clinical documents correspond to the patient and the at least the portion of the HL7 ADT message by comparing a creation time of the clinical documents to a time of the at least the portion of the HL7 ADT message and not electronically providing the clinical documents outside of a time threshold determined by the comparing.

\* \* \* \* \*